United States Patent
Hömberger et al.

(10) Patent No.: US 9,796,690 B2
(45) Date of Patent: Oct. 24, 2017

(54) PROCESS FOR PREPARING DIHYDROISOXAZOLE DERIVATIVES

(71) Applicant: Bayer CropScience Aktiengesellschaft, Monheim am Rhein (DE)

(72) Inventors: Günter Hömberger, Eppstein (DE); Mark James Ford, Wiesbaden-Breckenheim (DE); Andreas Hügel, Sulzbach (DE); Tomoki Tsuchiya, Lyon (DE)

(73) Assignee: Bayer CropScience Aktiengesellschaft, Monheim am Rhein (DE)

( * ) Notice: Subject to any disclaimer, the term of this patent is extended or adjusted under 35 U.S.C. 154(b) by 0 days.

(21) Appl. No.: 15/314,446

(22) PCT Filed: May 27, 2015

(86) PCT No.: PCT/EP2015/061623
§ 371 (c)(1),
(2) Date: Nov. 28, 2016

(87) PCT Pub. No.: WO2015/181189
PCT Pub. Date: Dec. 3, 2015

(65) Prior Publication Data
US 2017/0247345 A1  Aug. 31, 2017

(30) Foreign Application Priority Data

May 28, 2014 (EP) .................................. 14170155

(51) Int. Cl.
*C07D 261/04* (2006.01)
*A01N 43/80* (2006.01)

(52) U.S. Cl.
CPC ........... *C07D 261/04* (2013.01); *A01N 43/80* (2013.01)

(58) Field of Classification Search
None
See application file for complete search history.

(56) References Cited

U.S. PATENT DOCUMENTS 5,064,844 A  11/1991 O'Mahony et al.
2011/0223257 A1  9/2011 Zhao et al.

FOREIGN PATENT DOCUMENTS

| WO | WO-95/07897 | 3/1995 |
|---|---|---|
| WO | WO-2008/006561 | 1/2008 |
| WO | WO-2009/094445 | 7/2009 |
| WO | WO-2011/085170 | 7/2011 |
| WO | WO-2013/127808 | 8/2013 |

OTHER PUBLICATIONS

Extended European Search Report mailed on Sep. 3, 2014, for EP Patent Application No. 14170155.7 filed on May 28, 2014, 6 pages.
Hashimoto, S. et al. (1976). "The in Vitro Metabolism of 3-(1-Hydroxy-2-piperidinoethyl)-5-phenyl-isoxazole Citrate (31252-S) with Rabbit Liver Homogenate[1]," *Chem. Pharm. Bull* 24(8):1757-1764.
International Search Report mailed on Jul. 16, 2015, for PCT Patent Application No. PCT/EP2015/061623 filed on May 27, 2015, 10 pages.
Kanemasa, S. et al. (2000). "Synthesis of Hydroximoyl Chlorides from Aldoximes and Benzyltrimethylammonium Tetrachloroiodate (BTMA ICl$_4$)," *Tetrahedron* 56: 1057-1064.
Kidwai, M. et al. (2006). "K$_2$CO$_3$—Mediated Regioselective Synthesis of Isoxazoles and Pyrazolines," *Letters in Organic Chemistry* 3:135-139.
Liu, K.C. et al. (1980). "A Particularly Convenient Preparation of Benzohydroximinoyl Chlorides (Nitrile Oxide Precursors)," *J. Org. Chem.* 45:3916-3918.
Lohiya, S.B. et al. (Mar. 1986). "Reactions of a Chalcone with Hydroxylamine," *Indian Journal of Chemistry* 25B: 279-282.
Mohane, S.R. et al. (2009). "Synthesis and Biological Studies of Some Isoxazolines," *Asian Journal of Chemistry* 21(9): 7422-7424.
Radwan, M.A.A. et al. (2009). "Synthesis of some Pyridine, Thiopyrimidine, and Isoxazoline Derivatives Based on the Pyrrole Moiety," *Monatsh Chem* 140:229-233.
Shah, T. et al. (2007). "Synthesis and Antibacterial Studies of some Novel Isooxazoline Derivatives," *J. Serb. Chem. Soc.* 72(5): 443-449.
Tiwari, V. et al. (2010). "Benign Methodology and Improved Synthesis of 5-(2-chloroquinolin-3-yl)-3-phenyl-4,5-dihydroisoxazoline Using Acetic Acid Aqueous Solution Under Ultrasound Irradiation," *Ultrasonics Sonochemistry* 18:911-916.
Uno, H. et al. (1989). "Stepwise Intramolecular Cycloaddition of Nitrile Oxide Equivalents Derived from the Lewis Acid-promoted Reaction of 1-Nitroalkadienes and Allylic Stannanes," *J. Chem. Soc. Perkin Trans.* 1(2): 289-295.

*Primary Examiner* — Kamal Saeed
(74) *Attorney, Agent, or Firm* — Morrison & Foerster LLP

(57) ABSTRACT

The present invention relates to a novel process for preparing dihydroisoxazole derivatives.

4 Claims, No Drawings

PROCESS FOR PREPARING DIHYDROISOXAZOLE DERIVATIVES

CROSS REFERENCE TO RELATED APPLICATIONS

This application is the national stage of International Application No. PCT/EP2015/061623, filed internationally on May 27, 2015, which claims the benefit of European Application No. 14170155.7, filed May 28, 2014, the disclosures of which are hereby incorporated by reference in their entireties for all purposes.

The present invention relates to a novel process for preparing dihydroisoxazole derivatives.

Dihydroisoxazoles are valuable precursors of fungicidal or herbicidal active ingredients (US 2011/0223257 A1, WO 1995/007897 A1) or drugs like anti-cancer HDAC-inhibitors (WO 2008/006561 A1).

Known dihydroisoxazole derivatives are prepared by the treatment of an unsaturated ketone with hydroxamic acid derivative and subsequent ring closure (Scheme 1). Examples can be found in A. A. R. Mohamed and M. H. A. Eman, *Monatsh. Chem.*, 140, 229 (2009), T. Shah and V. Desai, *J. Serb. Chem. Soc.*, 72, 443 (2007), S. B. Lohiya and B. J. Ghiya, *Indian J. Chem.*, 25B, 279 (1996), S. R. Mohane, V. G. Thakare and B. N. Berad, *Asian J. Chem.*, 21, 7422 (2009), V. Tiwari, P. Ali and J. Meshram, *Ultrasonics Sonochem.*, 18, 911 (2011) or M. Kidwai, S. Kukreja and R. Thakur, *Lett. Org. Chem.*, 3, 135 (2006).

Scheme 1:

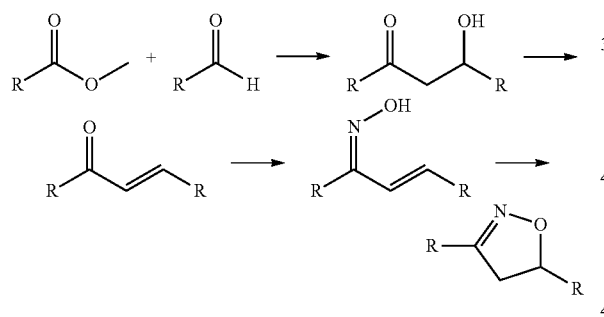

The disadvantage of this process is that regioisomers can appear and that multiple steps are necessary to yield the final product.

Alternatively dihydroisoxazole derivatives can be prepared by 1,3-dipole addition (Tetrahedron 2000, 56, 1057-1064; Chemical & Pharmaceutical Bulletin 1976, 24, 1757 or WO2011/085170) (Scheme 2):

Scheme 2:

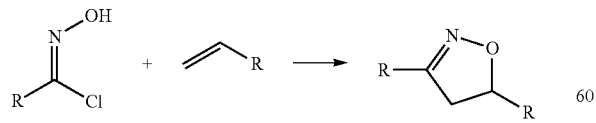

The disadvantage of this process is that a base has to be used which—depending on whether labile functionalities are present in the starting material—can cause side reactions. That generally leads to reduced yields if the reaction proceeds at all.

In the light of the prior art described above, it is an object of the present invention to provide a process that does not have the aforementioned disadvantages and hence gives a route to dihydroisoxazole derivatives in high yields.

The object described above was achieved by a process for preparing dihydroisoxazoles of the formula (I),

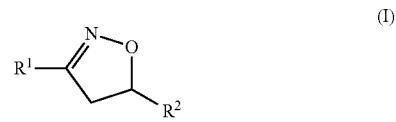

(I)

in which
$R^1$ is ketone (a)

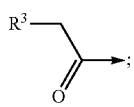

$R^2$ is phenyl which is optionally substituted once or more often independently of one another by halogen and $C_1$-$C_4$-alkylsulfonyloxy;
$R^3$ is selected from chlorine or bromine;
characterized in that hydroxyiminochlorides of the formula (II),

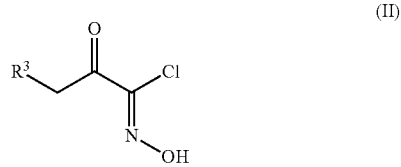

(II)

in which
$R^3$ is as defined above
are reacted via an elimination reaction to compounds of formula (III)

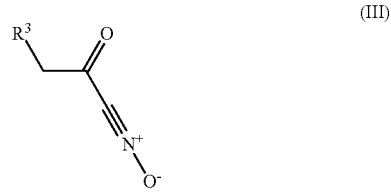

(III)

which are in situ transformed to compounds of formula (I) after the addition of (IV)

(IV)

in which $R^2$ is as defined above in the presence of a base, an acid and a solvent in acidic pH.

Surprisingly, the pyrazoles of the formula (I) can be prepared under the inventive conditions with good yields and in high purity, which means that the process according to the invention overcomes the abovementioned disadvantages of the preparation processes previously described in the prior art.

This reaction can be considered surprising as elimination of HCl from the compound of formula (II) would not be expected under conditions where the pH is below 7 (acidic). Quite the contrary, these conditions are normally used to prepare the hydoxyiminochloride, for example described in J. Org. Chem. 45, 3916 (1980) or U.S. Pat. No. 5,064,844. Thus it was extremely surprising to find that at pH levels significantly below 7, preferentially between pH 3 and pH 5, the 1,3-dipole (Formula III) can be generated efficiently and subsequently trapped with alkene derivatives to form compounds of formula (I).

Preference is given to a process according to the invention in which the definitions of the residues of the compounds of the formulae (I), (II), (III) and (IV) are defined as follows:
$R^1$ is ketone (a)

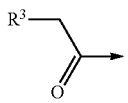

$R^2$ is phenyl substituted with chlorine and methylsulfonyloxy;
$R^3$ is chlorine.

General Definitions

Optionally substituted groups may be mono- or polysubstituted, where the substituents in the case of polysubstitutions may be the same or different.

In the definitions of the symbols given in the above formulae, collective terms were used which are generally representative of the following substituents:

Halogen: fluorine, chlorine, bromine and iodine and preferably fluorine, chlorine, bromine and more preferably chlorine.

Alkyl: saturated, straight-chain or branched hydrocarbyl radicals having 1 to 4 carbon atoms, for example (but not limited to) $C_1$-$C_4$-alkyl such as methyl, ethyl, propyl, 1-methylethyl, butyl, 1-methylpropyl, 2-methylpropyl, 1,1-dimethylethyl. This definition also applies to alkyl as part of a composite substituent, for example alkylsulphonyl, alkoxy.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

Process Description

The process is illustrated in Scheme 3:

Scheme 3

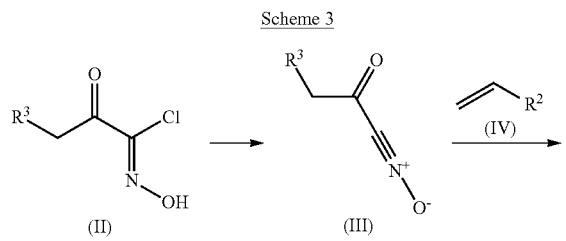

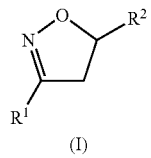

Hydroxyiminochlorides of the formula (II), are reacted via an elimination reaction to compounds of formula (III) which are in situ transformed to compounds of formula (I) after the addition of (IV) in the presence of a base, an acid and a solvent in acidic pH.

For the reaction according to the invention it is decisive to control the pH level. The reaction is conducted under acidic conditions by addition of a buffer system or by addition of a weak base to capture spontaneously eliminated HCl thereby ensuring that no further deprotonation of compounds of formula (IV), (III) or (I) occurs. Preferably the pH level is between pH 3 and pH 5, more preferably it is between pH 3.5 and pH 4.5.

The weak base can be for example taken from the group of hydrogen carbonates, like sodium hydrogencarbonate or potassium hydrogencarbonate, or from the group of hydrogenphosphates, like (di)sodium (di)hydrogenphosphate or (di)potassium (di)hydrogenphosphate or from the group of alkali salts of organic acids, like sodium acetate or sodium benzoate. Preferred is sodium hydrogencarbonate.

The buffer system consists of a weak acid and a salt of the weak acid, it can be for example taken from acetic acid/sodium acetate or acetic acid/ammonium acetate or formic acid/sodium formiate or dihydrogenphosphate/monohydrogenphosphate. Preferred is acetic acid/sodium acetate.

The reaction can be performed in a solvent, taken from the group of halogenalkanes like methylene chloride or 1,2-dichloroethane or from the group of aromatic compounds like benzene, toluene, xylene, chlorobenzene, dichlorobenzene or from the group of polar aprotic solvents like N,N-dialkylformamide, -acetamide, N-methylpyrrolidon, dimethylpropylene urea, tetramethyl urea or in nitriles like acetonitriles, propionitrile or butyronitrile, in alkohols like methanol, ethanol, n-propanol, iso-propanol, n-butanol or iso-butanol, in ethers like diethylether, tert.butylmethylether, diisopropylether, in ketones like acetone, methylisobutyl ketone in carboxylic esters like ethyl acetate, butyl acetate. The reaction can be performed in mixtures of these solvents. Preferably the reaction can be performed in acetonitrile, ethyl acetate or in a mixture thereof. Advantageously, the can reaction be performed in the presence of water.

The reaction can be performed in a temperature range from −10° C. to the boiling point of the solvent, which is used, preferable in the range from 0° C. to 50° C., more preferable in the range from 5° C. to 40° C.

Compounds of formula (II) are known and can be prepared as described in J. Org. Chem. 45, 3916 (1980) or U.S. Pat. No. 5,064,844.

Compounds of formula (IV) are well known. They are either commercially available or can be prepared according procedures described in standard literature like "Organic Synthesis", for example in Organic Synthesis 1928, 8, 84; Organic Synthesis 1948, 28, 31; Organic Synthesis 1953, 33, 62; Organic Synthesis 1966, 46, 89; Organic Synthesis 2006, 83, 45.

EXAMPLES

Preparation of 3-chloro-2-vinylphenyl methanesulfonate

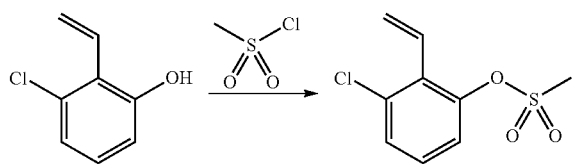

6 g (0.038 mol) of 3-chloro-2-vinylphenol, dissolved in 50 ml toluene, is cooled to 0-5° C. 4.4 g (0.043 mol) triethylamine is added and then a solution of 4.9 g (0.043 mol) methanesulfonic acid chloride in 5 ml toluene is added at 0-5° C. in 15 minutes. After stirring for 1 hour the reaction mixture is poured on ice. Phases are separated and the aqueous phase is extracted with 25 ml toluene. The combined organic phases are washed with 25 ml of water. The solvent is distilled of at 30° C. under vacuum and the residue is cristallised from heptane/tert.butylmethylether.

5 g of 3-chloro-2-vinylphenyl methanesulfonate with a purity of 95% is received (yield: 56%).

Preparation of 3-chloro-2-[3-(chloroacetyl)-4,5-dihydro-1,2-oxazol-5-yl]phenyl methanesulfonate

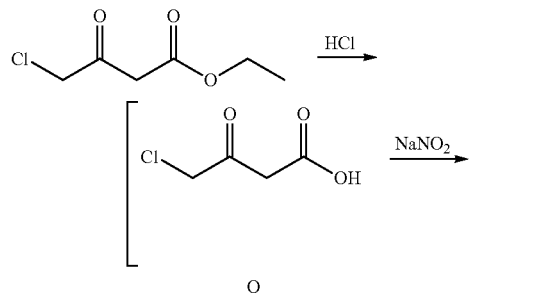

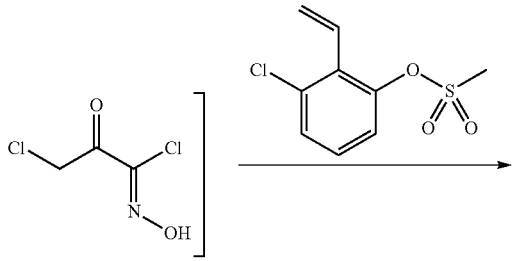

-continued

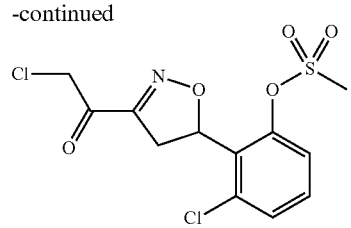

A mixture of 92 g (0.55 mol) ethyl-4-chloro acetoacetate and 542 g 37% hydrochloric acid is stirred at 25° C. for 24 hours. The mixture is concentrated to 320 g at 40° C. under vacuum and cooled to 5° C. 215 g of 20% sodium hydroxide is added, so that the internal temperature did not exceed 10° C. The mixture is cooled to 0° C. and 159 g of a 20% solution of sodium nitrite is added during 15 minutes. Gas evolution is observed and finally)-1-chloro-3-(hydroxyimino)acetone precipitates. After 30 minutes stirring at 0° C., the mixture is extracted once with 360 ml ethyl acetate and twice with 120 ml ethyl acetate each. To the combined organic phases is added 51 g sodium hydrogencarbonate and 29 g water. 37.6 g of chlorine gas is introduced during 30 min at a temperature of 0-5° C. After stirring for 30 min at 0-5° C. half of the mixture is separated and to this is added 46.4 g of 3-chloro-2-vinylphenyl methanesulfonate (0.199 mol). the mixture is warmed to 35° C. and stirred, while the pH of the mixture is adjusted between 4.3 to 4.5 by addition of a 25% aqueous solution of potassium hydrogencarbonate. The second half of the chloro oxime solution is added after 1 hour. Stirring at 35° C. is continued for further 4 hours, while the pH is kept between 4.3 and 4.5 with a total amount of 129 g 25% potassium hydrogencarbonate. The mixture is cooled to 20° C. and the phases are separated. The organic phase is concentrated to 106 g at 30° C. under vacuum. 160 ml of ethanol is added to the residual oil and the mixture is heated to 70° C. then the mixture is slowly cooled to 20° C. with intermediate seeding. The product precipitates and stirring is continued at 0° C. for 1 hour. The product is filtered off, washed with cold ethanol and dried at 30° C. in vacuum.

55.6 g of 3-chloro-2-[3-(chloroacetyl)-4,5-dihydro-1,2-oxazol-5-yl]phenyl methanesulfonate with 97% purity were received (yield: 77%).

The invention claimed is:
1. A process for preparing a compound of formula (I),

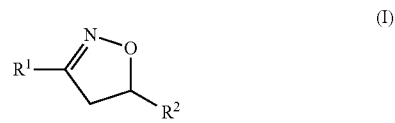

in which
$R^1$ is ketone (a)

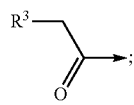

$R^2$ is phenyl which is substituted once or more often independently of one another by halogen or $C_1$-$C_4$-alkylsulfonyloxy; and R³ is selected from the group consisting of chlorine and bromine;

comprising reacting a compound of formula (II),

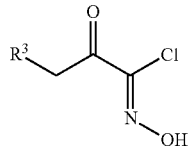

in which
R³ is as defined above;
via an elimination reaction to form a compound of formula (III)

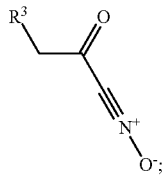

and reacting the compound of formula (III) in situ with a compound of formula (IV)

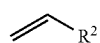

in which R² is as defined above in the presence of a base, an acid and a solvent in acidic pH to form the compound of formula (I).

2. The process according to claim 1, characterized in that R¹ is ketone (a)

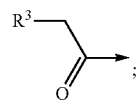

R² is phenyl substituted with chlorine and methylsulfonyloxy; and
R³ is chlorine.

3. The process according to claim 1 in which the pH is 3.5 to 4.5.

4. The process according to claim 1 in which a buffered solution comprising acetic acid and sodium acetate is used.

* * * * *